United States Patent
Hugg et al.

(10) Patent No.: US 12,383,216 B2
(45) Date of Patent: Aug. 12, 2025

(54) STEREOTACTIC MBI-GUIDED BIOPSY USING A VARIABLE-ANGLE SLANT-HOLE COLLIMATOR

(71) Applicant: Smart Breast Corporation, Sherman Oaks, CA (US)

(72) Inventors: James W. Hugg, Tyler, TX (US); Bradley E. Patt, Sherman Oaks, CA (US)

(73) Assignee: Smart Breast Corporation, Sherman Oaks, CA (US)

( * ) Notice: Subject to any disclaimer, the term of this patent is extended or adjusted under 35 U.S.C. 154(b) by 0 days.

(21) Appl. No.: 18/751,223

(22) Filed: Jun. 22, 2024

(65) Prior Publication Data
US 2024/0423569 A1 Dec. 26, 2024

Related U.S. Application Data

(60) Provisional application No. 63/522,890, filed on Jun. 23, 2023.

(51) Int. Cl.
*A61B 6/03* (2006.01)
*A61B 6/04* (2006.01)
(Continued)

(52) U.S. Cl.
CPC .............. *A61B 6/502* (2013.01); *A61B 6/037* (2013.01); *A61B 6/12* (2013.01); *A61B 6/4291* (2013.01);
(Continued)

(58) Field of Classification Search
CPC . A61B 6/037; A61B 6/4291; G21K 1/02-046
See application file for complete search history.

(56) References Cited

U.S. PATENT DOCUMENTS

| 4,419,585 A | 12/1983 | Strauss |
| 9,711,251 B2 | 7/2017 | Lee |

(Continued)

OTHER PUBLICATIONS

Moore, R. H., et al., A Variable Angle Slant-Hole Collimator, J Nucl Med 24: 61-65, 1983.

*Primary Examiner* — Colin T. Sakamoto
(74) *Attorney, Agent, or Firm* — BARTONY & ASSOCIATES, LLC

(57) ABSTRACT

A molecular imaging method for guidance in biopsy or surgical procedures includes selecting and inputting two different slant angles for stereotactic molecular imaging of a hot spot, positioning a patient to whom a radiotracer has been administered in a molecular imaging system including a solid-state gamma camera and a variable-angle square hole (VASH) collimator, acquiring two stereotactic molecular images with the VASH collimator, each of the two stereotactic molecular images being acquired when the VASH collimator is adjusted to a different one of the two different slant angles, calculating a 3D position of a hot spot, and performing a molecular image-guided biopsy procedure on the basis of the calculated 3D position. In acquiring the two stereotactic molecular images, the VASH collimator is positioned such that the two different slant angles are in a plane generally parallel (that is, within 30 degrees of parallel) to a coronal plane of the patient.

14 Claims, 7 Drawing Sheets

(51) Int. Cl.
    *A61B 6/12*     (2006.01)
    *A61B 6/42*     (2024.01)
    *A61B 6/50*     (2024.01)
    *G06T 7/00*     (2017.01)
    *G16H 50/20*    (2018.01)
    *A61B 10/00*    (2006.01)

(52) U.S. Cl.
    CPC ........... *G06T 7/0012* (2013.01); *G16H 50/20*
        (2018.01); *A61B 6/0414* (2013.01); *A61B*
        *10/0041* (2013.01); *G06T 2207/30068*
        (2013.01); *G06T 2207/30096* (2013.01)

(56) References Cited

U.S. PATENT DOCUMENTS

| | | |
|---|---|---|
| 10,617,382 B2 | 4/2020 | Hugg |
| 10,631,819 B2 | 4/2020 | Hugg |
| 11,096,636 B2 | 8/2021 | Kross |
| 11,526,985 B1* | 12/2022 | Welch ................ G06T 5/73 |
| 2012/0108948 A1* | 5/2012 | Jansen ................ G21K 1/025 |
| | | 250/515.1 |
| 2016/0296186 A1* | 10/2016 | Hugg ................ A61B 6/502 |
| 2017/0040077 A1* | 2/2017 | Lee ................ G21K 1/04 |
| 2019/0388041 A1* | 12/2019 | Kross ................ A61B 6/12 |
| 2023/0384467 A1* | 11/2023 | Cherlin ................ G01T 1/249 |

* cited by examiner

}36

34

} 15

32

15

STEREOTACTIC MBI-GUIDED BIOPSY USING A VARIABLE-ANGLE SLANT-HOLE COLLIMATOR

CROSS-REFERENCE TO RELATED APPLICATIONS

This application claims benefit of U.S. Provisional Patent Application Ser. No. 63/522,890 filed Jun. 23, 2023, the disclosure of which is incorporated herein by reference.

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

In 1990, the radiopharmaceutical imaging agent CARDIOLITE® (injectable Technetium Tc99m-Sestamibi) was cleared by the U.S. Food and Drug Administration (FDA) for Single-Photon Emission Computed Tomography (SPECT) myocardial perfusion imaging. As cardiologists gained experience with this mitochondrial tracer, they reported anecdotally that breast tumors also take up Sestamibi. This led to a new application in breast cancer detection known as scintimammography, which generally involved imaging the patient with a whole-body gamma camera in a prone position with the breasts pendant or lightly compressed. Limitations of scintimammography were soon realized. In that regard, high radiation doses were required, and inadequate spatial resolution made the technique less effective for tumors smaller than one centimeter in diameter.

Techniques were then explored for using smaller gamma cameras dedicated to breast imaging. A number of such techniques can approach the breast more closely, so that spatial resolution can be improved, and smaller tumors detected. Both Positron Emission Tomography (PET) and planar Single-Photon Emission (SPE) imaging were developed and enjoyed some technical and commercial success. Radiation dose to the patient and technologist, however, remained too high for widespread use. In the early 2000's a new solid-state pixelated digital gamma photon detector became available for experimental applications. Working with the Mayo Clinic in Rochester, MN, both General Electric Healthcare and Gamma Medica developed cadmium-zinc-telluride (CdZnTe or CZT) gamma cameras for breast cancer imaging. The technique developed at the Mayo Clinic was named Molecular Breast Imaging (MBI), a term adopted now by most clinical users and all commercial vendors. In recent improvements, the whole-body radiation dose for supplemental screening or diagnosis has been significantly reduced on commercial CZT systems so that it is nearly equivalent to that of screening mammography or digital breast tomosynthesis (DBT).

SUMMARY

In one aspect, a molecular imaging method for guidance of a biopsy or a surgical procedure includes selecting and inputting two different slant angles for stereotactic molecular imaging of a hot spot, positioning the patient to whom a radiotracer has been administered in a molecular imaging system including a solid-state gamma camera and a variable-angle slant hole (VASH) collimator, acquiring two stereotactic molecular images with the VASH collimator, each of the two stereotactic molecular images being acquired when the VASH collimator is adjusted to a different one of the two different slant angles, calculating a 3D position of a hot spot, and performing a molecular image-guided biopsy procedure on the basis of the calculated 3D position. In acquiring the two stereotactic molecular images, the VASH collimator is positioned such that the two different slant angles are in a plane generally parallel (that is, within 30 degrees of parallel) to a coronal plane of the patient. In a number of embodiments, the VASH collimator is positioned such that the two different slant angles are in a plane within 5 degrees of parallel to the coronal plane of the patient. The two different slant angles may, for example, have an angular spread of 10 to 60 degrees.

The VASH collimator may, for example, include a stack of thin leaves (for example, formed from a metal such as tungsten). Each of the leaves comprising an array of holes (for example, square holes) and a mechanical mechanism for positioning the leaves to align the holes at the slant angles.

The molecular imaging system may further include more than one solid-state gamma camera (for example, a second or third solid-state gamma camera). Each gamma camera includes one of a parallel-hole collimator, a slant-hole collimator, a focusing collimator, a VASH collimator, and a multiple pinhole collimator.

The performing of the molecular image-guided procedure may include compressing tissues via a compression paddle which includes an aperture and the movement of a second solid-state gamma camera, which is movable in and out of connection with the compression paddle, to allow access to the aperture. In a number of embodiments, performing the molecular image-guided procedure further includes acquiring a verification molecular image of a pathway to approach the hot spot. The method may further include placing a cavity marker in a breast biopsy procedure and acquiring a post-biopsy mammogram.

The molecular imaging method may, for example, include molecular breast imaging (MBI), single photon emission (SPE) planar imaging, single photon emission computed tomography (SPECT), or positron emission tomography (PET).

Electronic circuitry may be in communicative connection with the solid-state gamma camera and with the VASH collimator. The electronic circuitry may be configured to control slant angles of the VASH collimator and to control the solid-state gamma camera to acquire the molecular images at each of the two different slant angles, which are input into the electronic circuitry. The electronic circuitry may further be configured to calculate the 3D position of the hot spot from the molecular images at each of the two different slant angles.

In another aspect, a molecular imaging system for guidance of a biopsy or a surgical procedure includes a solid-state gamma camera, a VASH collimator; and electronic circuitry in communicative connection with the solid-state gamma camera and with the VASH collimator. The electronic circuitry is configured to control slant angles of the VASH collimator and to control the solid-state gamma camera to acquire a molecular image at each of two different slant angles. The electronic circuitry is further configured to calculate a 3D position of a hot spot from the molecular images at each of the two different slant angles. The VASH collimator is positioned such that the two different slant angles are in a plane generally parallel to a coronal plane of a patient. In a number of embodiments, the two different slant angles have a spread of 10 to 60 degrees.

In a number of embodiments, the VASH collimator includes a stack of thin leaves. Each of the leaves includes an array of holes (for example, square hole). The VASH collimator further includes a mechanism for positioning the stack (that is, each of the leaves of the stack) to align the holes at the two different slant angles.

The molecular imaging system may include at least one other gamma camera. The at least one other gamma camera includes one of a parallel-hole collimator, a slant-hole collimator, a focusing collimator, a VASH collimator, and a multiple pinhole collimator.

The system may further include a compression paddle, which includes an aperture, and a second solid-state gamma camera. The second solid-state gamma camera is movable in and out of connection with the compression paddle, such that when the second solid-state gamma camera is moved out of connection with the compression paddle, access is provided to the aperture.

The molecular imaging system may, for example, functions as, includes or is a molecular breast imaging (MBI) system, single photon emission (SPE) planar imaging system, a single photon emission computed tomography (SPECT) system, or a positron emission tomography (PET) system.

In a further aspect, a molecular imaging method for guidance of a biopsy or a surgical procedure includes selecting and inputting two different slant angles for stereotactic molecular imaging of a hot spot, positioning a patient to whom a radiotracer has been administered in a molecular imaging system including a solid-state gamma camera and a VASH collimator, acquiring two stereotactic molecular images with the VASH collimator, each of the two stereotactic molecular images being acquired when the VASH collimator is adjusted to a different one of the two different slant angles, calculating a 3D position of a hot spot, performing a molecular image-guided biopsy procedure on the basis of the calculated 3D position, and acquiring a confirmation molecular image of at least one of one or more samples taken and a procedure cavity. The two different slant angles may, for example, have an angular spread of 10 to 60 degrees.

The variable-angle slant hole (VASH) collimator may, for example, include a stack of thin leaves (for example, formed from a metal such as tungsten). Each of the leaves comprising an array of holes (for example, square holes) and a mechanical mechanism for positioning the leaves to align the holes at the slant angles.

In a number of embodiments, electronic circuitry is in communicative connection with the solid-state gamma camera and with the VASH collimator. The electronic circuitry may be configured to control slant angles of the VASH collimator and to control the solid-state gamma camera to acquire the molecular images at each of the two different slant angles, which are input into the electronic circuitry. The electronic circuitry being further be configured to calculate the 3D position of the hot spot from the molecular images at each of the two different slant angles.

The present devices, systems, and methods, along with the attributes and attendant advantages thereof, will best be appreciated and understood in view of the following detailed description taken in conjunction with the accompanying drawings.

DETAILED DESCRIPTION

Figure 1:
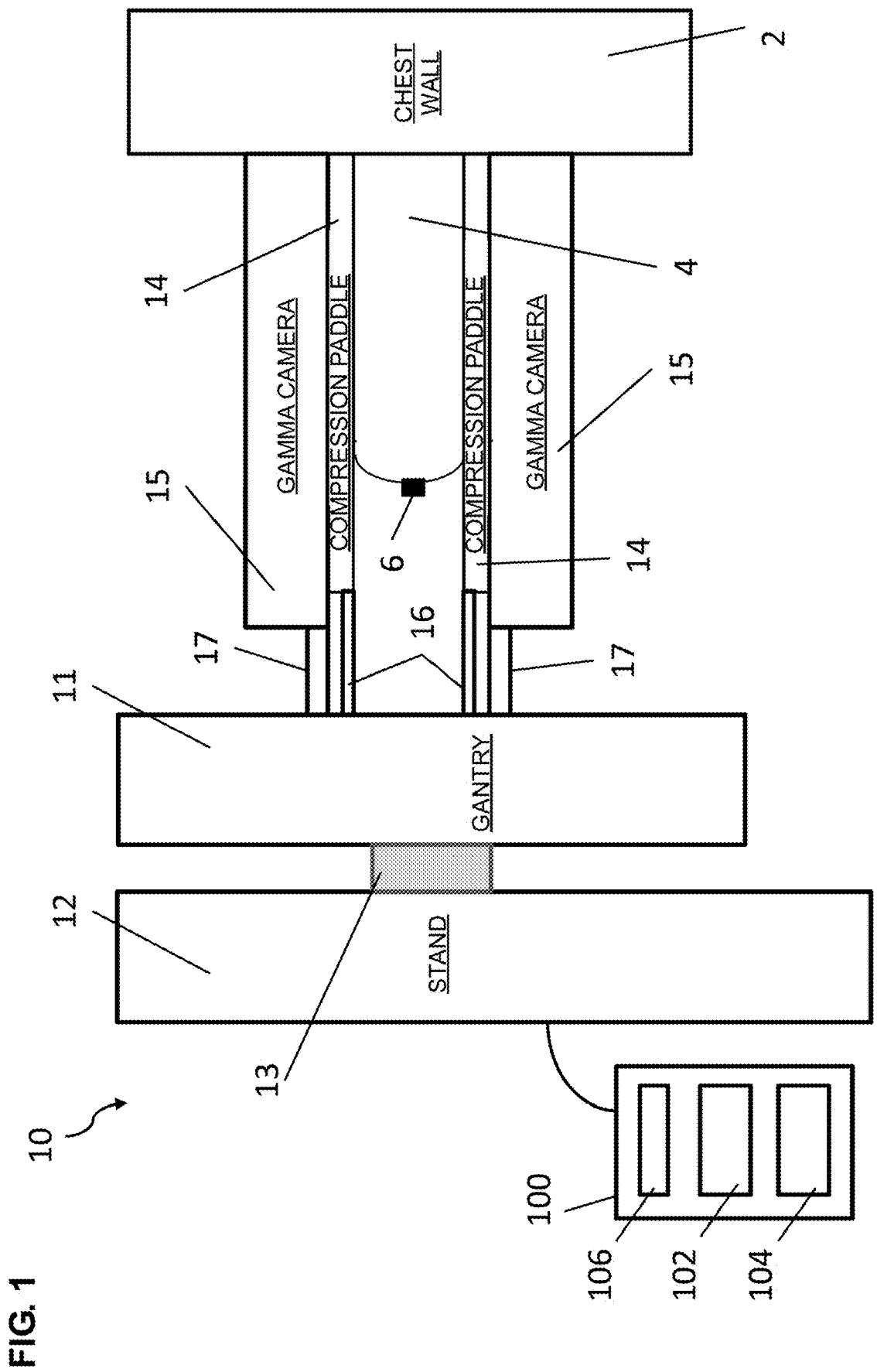
FIG. 1 illustrates a side, schematic view of an embodiment of an MBI system with gantry, gamma cameras, and electronic circuitry.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "an algorithm" includes a plurality of such algorithms and equivalents thereof known to those skilled in the art, and so forth, and reference to "the algorithm" is a reference to one or more such algorithms and equivalents thereof known to those skilled in the art, and so forth. Recitation of ranges of values herein are merely intended to serve as a shorthand method of referring individually to each separate value falling within the range. Unless otherwise indicated herein, each separate value, as well as intermediate ranges, are incorporated into the specification as if individually recited herein. All methods described herein can be performed in any suitable order unless otherwise indicated herein or otherwise clearly contraindicated by the text.

The terms "electronic circuitry", "circuitry" or "circuit," as used herein include, but are not limited to, hardware, firmware, software, or combinations of each to perform a function(s) or an action(s). For example, based on a desired feature or need, a circuit may include a software-controlled microprocessor, discrete logic such as an application specific integrated circuit (ASIC), or other programmed logic device. A circuit may also be fully embodied as software. As used herein, "circuit" is considered synonymous with "logic." The term "logic", as used herein includes, but is not limited to, hardware, firmware, software, or combinations of each to perform a function(s) or an action(s), or to cause a function or action from another component. For example, based on a desired application or need, logic may include a software-controlled microprocessor, discrete logic such as an application specific integrated circuit (ASIC), or other programmed logic device. Logic may also be fully embodied as software.

The term "processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random-access memory (RAM), read-only memory (ROM), programmable read-only memory (PROM), erasable programmable read only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

The term "controller," as used herein includes, but is not limited to, any circuit or device that coordinates and controls the operation of one or more input and/or output devices. A controller may, for example, include a device having one or more processors, microprocessors, or central processing units capable of being programmed to perform functions.

The term "software," as used herein includes, but is not limited to, one or more computer readable or executable instructions that cause a computer or other electronic device to perform functions, actions, or behave in a desired manner. The instructions may be embodied in various forms such as routines, algorithms, modules, or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, or the desires of a designer/programmer or the like.

Embodiments of methods and systems hereof provide for guiding surgical interventions using molecular imaging, such as MBI-guided breast biopsy. Streamlined methods and systems hereof use a variable-angle slant-hole (VASH) collimator to acquire two stereotactic images and measure the 3D location of a visualized hot spot. Such a method is a significant improvement over previous methodologies. Although the basic design of a VASH collimator has been known for over four decades, no practical use has been made of this unique collimator design. However, the Jefferson Lab, working with Dilon Technologies, designed and built a practical working prototype and demonstrated an application: limited angle tomographic imaging using multiple VASH collimators. This present application will teach a novel, non-obvious new application of the VASH collimator, namely MBI-guided biopsy or surgery.

In a number of embodiments hereof, a VASH collimator is used to acquire two "stereotactic" molecular breast images, selecting two angles between −30 and +30 degrees from the axis between the upper and lower gamma cameras and with a spread between the two angles of 15 to 60 degrees. A computer then calculates a 3D (x, y, z) spatial position of the target hot spot(s). After the hot spots have been sampled by needle biopsy or surgery, MBI can be used to confirm that the sampling has been adequate.

Devices, systems, and methods hereof may, for example, be used in connection with non-invasive molecular imaging such as molecular breast imaging (MBI), single photon emission (SPE) planar imaging, single photon emission computed tomography (SPECT), or positron emission tomography (PET). In general, molecular imaging is a branch of medical imaging that concentrates upon imaging molecules of medical interest within a patient.

Molecular breast imaging (MBI) is described herein in a number of representative examples of MBI-guided biopsy using a VASH collimator via the devices, systems, and methods hereof for molecular imaging. However, one skilled in the art appreciates that such applications of devices, systems and methods hereof to MBI are representative examples and that the principles of the devices, systems, and methods hereof are equally applicable to other molecular imaging techniques such as SPE, SPECT, and PET imaging. Moreover, those skilled in the art appreciate that organs/regions of interest other than the breast (such as the prostate, the brain, etc.), or diseases other than cancer (such as epilepsy, multiple sclerosis, etc.), or surgical intervention procedures other than biopsy also may benefit from using the devices, systems and/or methods hereof.

Advantages provided by the devices, systems, and methods hereof include, but are not limited to a streamlined clinical protocol for performing breast biopsy under either ultrasound or MBI guidance. The commercial MBI-guided biopsy systems have proved to be clumsy and required lengthy protocols. While a number of such systems worked and provide reasonable results, healthcare providers were unhappy with the hardware, software, and/or clinical protocols used to implement biopsy guidance. In the devices, systems, and methods hereof hardware and software are significantly simplified and clinical protocols streamlined for imaging-guided surgeries (such as MBI-guided surgeries), including biopsies.

Another approach to MBI-guided biopsy is to tilt the upper detector of a two-detector system by about 15 degrees in the AP (Anterior-Posterior) direction to achieve a stereoscopic view. An air gap is created between the gamma detector and the breast with the largest gap in the nipple direction. Limitations in that technique include 1) spatial resolution depends upon distance of the collimator from the organ and hot spot being imaged, so the larger the air gap between the detector and the breast, the poorer the resolution; and 2) the stereotactic effect is diminished with the upper detector tilted 15 degrees and the bottom detector at 0 degrees, for a total angular spread of only 15 degrees. In embodiments hereof, two images are compared, desirably with a total angular spread of at least 15 degrees and up to 60 degrees. A larger parallax shift produces more accurate 3D positions of the hot spot(s).

An embodiment of a system and method hereof 1) places one or more (for example, two) detectors as close as possible to the breast to maintain the highest spatial resolution; 2) provides a 15-60 degree stereoscopic spread generally in the Left-Right or medial-lateral direction (that is, within 30 degrees of parallel to the coronal plane of the patient) that produces much more accurate 3l) position determinations of the hot spot(s); and 3) requires no detector or collimator frame movement at all for the two verification images (in that regard, only housed or internal components move). A second detector (when present; for example, an upper detector) may remain in its tilted, out-of-the-way position for both verification images, which can be acquired by the first (for example, bottom) detector alone with a VASH collimator.

If the results of the mammogram examination are equivocal or require further study before a clinical plan can be determined, the patient may be referred for molecular breast imaging (MBI) for secondary diagnosis. Once a mammogram has shown that a woman has dense breast tissue, the referring physician may decide to forego annual screening mammography and send the woman instead for an annual MBI screening study. It should be noted that the National Comprehensive Cancer Network [NCCN] recommends MBI for supplemental breast cancer screening in women with dense breasts. In still other cases, one or more hot spots may be found on MBI and the woman may undergo neo-adjuvant chemotherapy to treat the hot spots before any potential surgical intervention. MBI may be used to monitor the progress of such therapy. Another application for MBI is to guide surgical intervention, such as biopsy or lumpectomy of the one or more hot spots detected by MBI.

In supplemental diagnosis or screening MBI, a small dose of Tc99m-Sestamibi or Tc99m-Tetrofosmin, which are radiopharmaceuticals taken up by cells with a high concentration of mitochondria, is injected intravenously (i.v.) into the woman and the molecules of the agent are preferentially taken up by the abundant mitochondria in breast cancer cells. The radiologist may make a trade-off between radiation dose and imaging time in choosing how much radiotracer to inject. The Mayo Clinic has demonstrated that MBI screening is feasible at a dose of 4 mCi Tc99m-Sestamibi (currently an off-label use).

In Positron-Emission Mammography (PEM), the tracer is typically fluorodeoxyglucose ($^{18}$F) or FDG (a radiopharmaceutical which is a marker for tissue uptake of glucose). The patient is typically positioned in a chair with one breast lightly compressed (about ⅓ the force needed for x-ray mammography) to immobilize the breast between two parallel-opposed small gamma cameras. The patient may also be positioned in lateral decubitus, which is lying on her side on a bed or table. MBI imaging typically begins within 5 minutes or less after i.v. injection of Tc99m tracer. However, in PEM the patient may rest for an hour or more before imaging to allow washout from background tissue.

In common clinical practice, the two breasts are generally imaged one at a time and in two orientations each: generally parallel to a body-axis line of view called the craniocaudal or CC view, and along an approximately 40-60 degrees offset line of view imaging the breast and axilla called the medio-lateral oblique or MLO view. In some circumstances, an approximately 90 degree offset line of view called the lateral view will be substituted for the MLO view. There is no technical requirement to image the two breasts separately or in only two standard MMG views.

After performing an MBI screening or secondary diagnostic examination, a qualified breast radiologist will interpret the molecular images and determine whether a biopsy of any suspicious hot spot should be performed to determine if the hot spot is malignant. If the radiologist determines that a biopsy is required, then a second-look ultrasound may be performed to guide biopsy needle sampling of the suspicious hot spot if it is visible. The ultrasound-guided biopsy may be performed while the breast is still mildly compressed in the MBI system. The advantage is that the biopsy cavity and extracted tissue samples may be imaged by MBI immediately following the biopsy to confirm the accuracy of the biopsy sampling.

An MBI-guided biopsy is preferable to an MRI-guided biopsy. MRI-guided biopsy is a lengthy and expensive procedure, often uncomfortable and distressing to the patient who must remain prone with arms raised above her head for a long time (up to two hours). An MBI-guided biopsy is quicker, less stressful, and less expensive for the patient and the imaging center. Breast MRI can suffer from too many biopsy targets; many hot spots are visualized and not all can be biopsied. MBI is more specific.

FIG. 1 illustrates an embodiment of an MBI system 10 used in connection with the methodologies hereof. FIG. 1 shows a cross-sectional side view with gantry 11 on the left and the patient's chest wall 2 on the right with breast 4 and nipple 6 positioned toward gantry 11. Thin compression paddles 14 (for example, formed from a transparent polymeric or plastic material such as an acrylic, or carbon fiber, or other materials known to those skilled in the art) directly contact and immobilize breast 4. Compression paddles 14 are not required for screening or diagnostic MBI but the upper one is typically required for MBI-guided biopsy. In a preferred embodiment, the upper paddle will have a rectangular window into which a plastic grid can be snapped into place. Each aperture in the grid will accommodate a plastic block perforated with (typically) a 3×3 array of holes through which the biopsy needle can pass. If one or more compression paddles 14 are not present in the MBI system 10 then one or more gamma cameras 15 may directly contact breast 4 and provide the mild compression needed to immobilize the breast.

Those skilled in the art will appreciate that electronic circuitry 100, including, for example, a processor system 102 in operative connection with a memory system 104, may include software including one or more algorithms stored in memory system 104 and executable by processor system 102 to operate as a control system or controller to independently control motion of the gantry 11, rotor 13, gamma cameras 15, and compression paddles 14. Electronic circuitry 100 may also operate to acquire, process, and display the gamma emission images collected during the MBI examination. Alternatively, manual control can be used to adjust the positions of gantry 11, rotor 13, gamma cameras 15, and compression paddles 14 and to control image acquisition by the cameras 15. Processor system 102 (which may, for example, include one or more processors and/or microprocessors) of electronic circuitry 100 may also execute software stored in memory system 104 including one or more models/algorithms that implement one or more algorithms or sub-algorithms such as algorithm 600 described herein. As known in the computer arts, an input/output system 106 may be in operative connection with processor system 102 and memory system 104 to acquire data input from MBI system 10 and/or one or more users and to output data/information. Although software algorithms hereof may be executed via electronic circuitry 100 of system 10, one skilled in the art appreciates that such algorithms may, for example, be stored and executed separately (for example, via a separate computer or an embedded microchip) or that storage of such algorithms and execution thereof may be distributed over a number of devices or systems.

As known in the art, the gantry assembly may, for example, include gantry 11 which supports compression paddles 14 and gamma cameras 15. Gantry 11 may, for example, be rotatably connected by a rotor 13 to a stand 12 which supports the weight of the gantry assembly and provides power and data transmission between the gamma cameras 15 and the electronic circuitry 100.

In a number of embodiments, two gamma cameras 15 are used in system 10, but a single camera can be used to reduce system cost as a trade-off for higher dose or longer exam time. Alternatives with more than two small cameras may also be used.

As known to those skilled in the art of molecular imaging, gamma cameras 15 include a collimator and a detector assembly. The collimator will be further discussed with reference to FIGS. 3B through 4B. In a preferred embodiment, the collimator may have a square parallel-hole core and the detector assembly may be an array of square pixelated CZT detectors. The collimator may, for example, include parallel-hole, slant-hole, focusing (convergent or divergent), multiple-pinhole collimators, or Compton camera (a form of "electronic collimation"). For pixelated detectors, square-hole collimators are preferred, but traditional hexagonal-hole collimators can also be used (although they are not as efficient). Alternatively, detector assembly of gamma cameras 15 may include a scintillator (pixelated or monolithic) and an array of photodetectors, such as vacuum photomultiplier tubes (PMTs), position-sensitive PMTs-PSPMTs, avalanche photodiodes (APDs), or solid-state photomultipliers (also called silicon photomultipliers or SiPMs) and the like.

System 10 of FIG. 1 incorporates a number of components known in the art, but includes several developments that provide significant advantages. First, the requirement for pixel-registered square-hole collimators can be relaxed in practice. The present inventors have found that pixel registration (that is, spatially matching one collimator hole with one detector pixel) is not critical and efforts to fine tune the collimator positioning with respect to the pixelated detector waste manufacturing and servicing time. That surprising observation is not an obvious finding. In fact, it goes directly against conventional wisdom which assumes that pixels and collimator holes must be nearly perfectly aligned and thus makes pixel registration a requirement. Through careful experimentation, it was discovered by the present inventors that precise pixel-registration is not a critical requirement.

A second advantage arises from the requirement in existing systems and methods that the slant holes of a VASH collimator be angled towards chest wall tissue. However, a distinct advantage is provided by left-right or medial-lateral oriented (see FIGS. 4A and 4B) variable angles for stereotactic biopsy with MBI-guidance. A particular advantage is the ability to place a VASH collimator as close as possible to the chest wall to maximize the volume of visible breast tissue. The mechanisms for varying the slant angle are best located on the right and left (that is, lateral) edges of a VASH collimator, where they do not interfere with patient positioning. If the slant holes are slanted toward the chest wall for one stereo image, the second stereo image would necessarily be slanted away from the chest wall, thus not imaging a substantial volume of tissue next to the chest wall. Only hot spots located within tissue imaged by both stereo views can be assigned a 3D position.

Figure 4A:
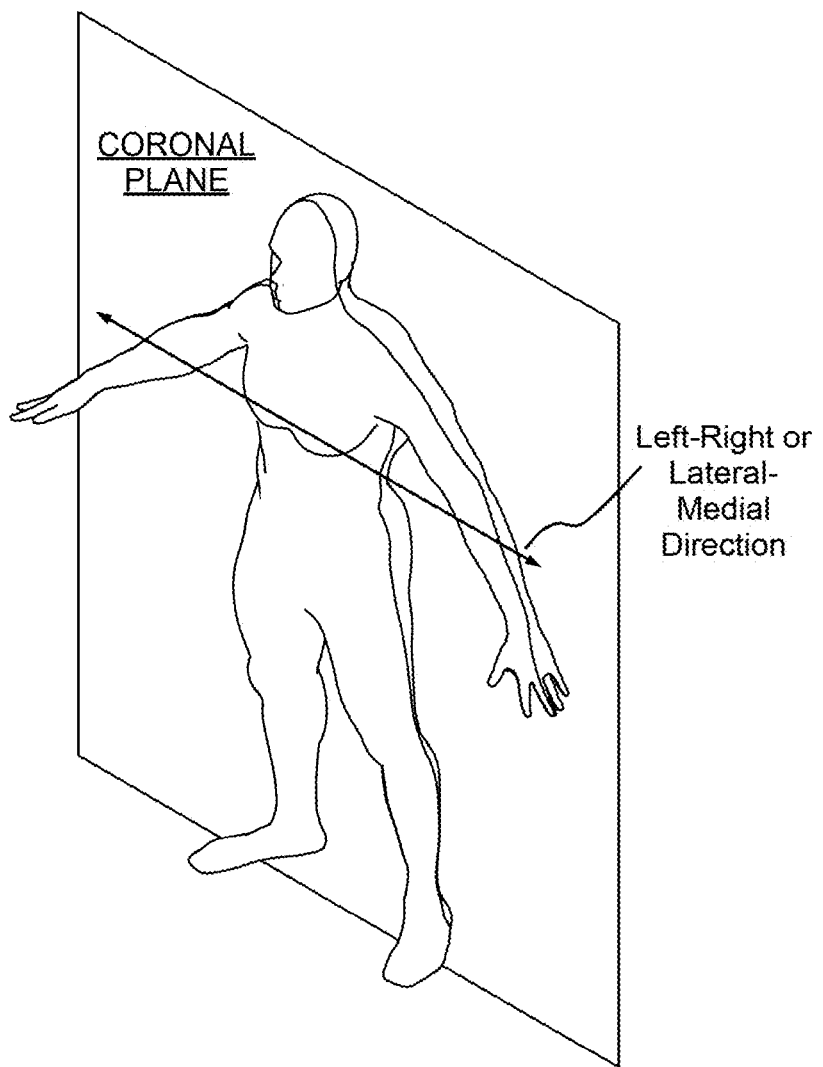
FIG. 4A illustrates a perspective view of a patient showing a representation of the coronal plane and left-right or lateral-medial direction.
Figure 4B:
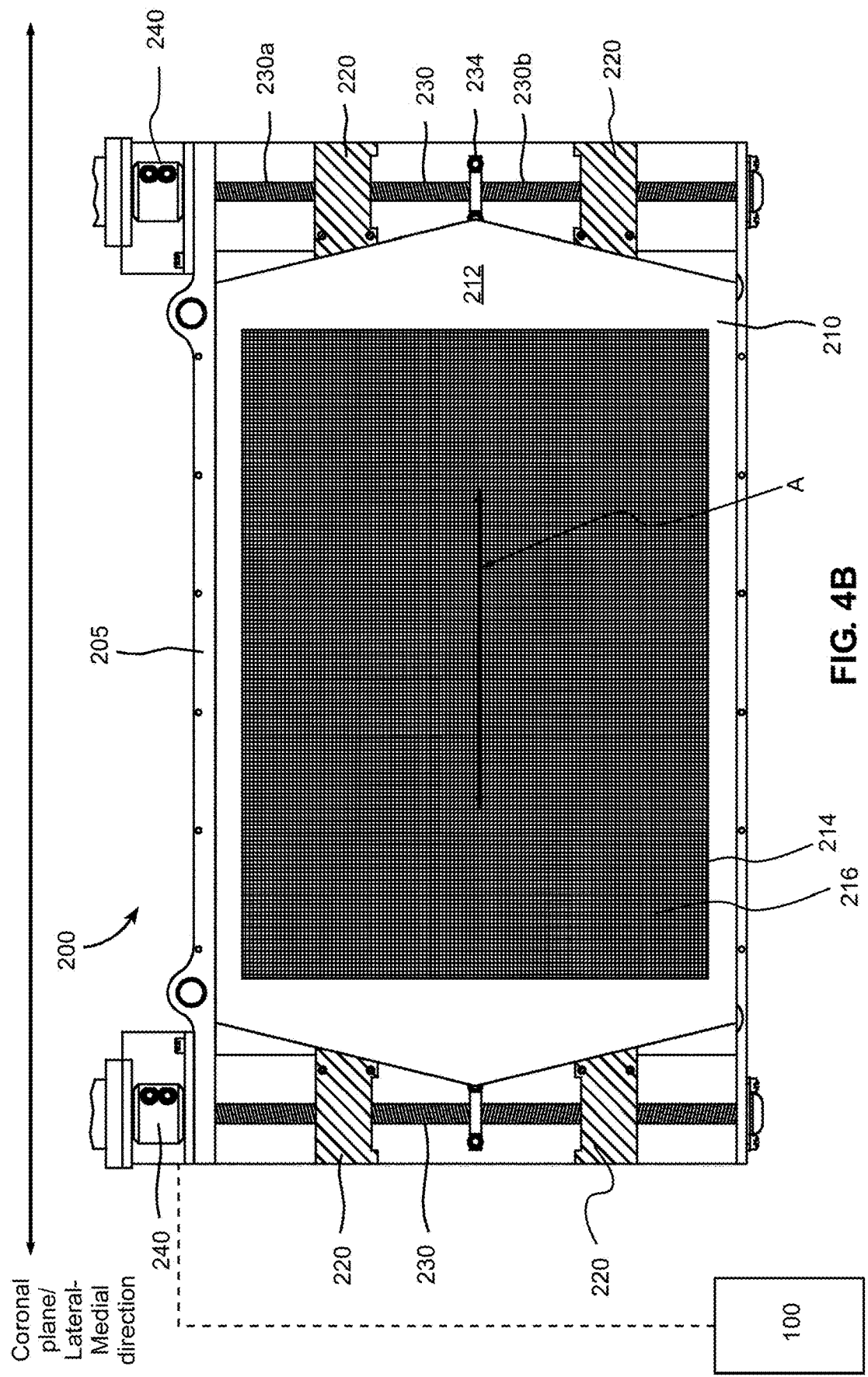
FIG. 4B is an illustration (top view) of an embodiment of a VASH collimator for use herein wherein the arrow illustrates the general direction of variability in slant angle.

A patented theoretical embodiment of a VASH collimator includes slantable alignment pins. However, the required thin, slantable alignment pins may be easily distorted and break if used to drive a VASH collimator to varying slant angles. An embodiment of a VASH collimator for use herein (as shown in FIG. 4B) is more robust.

Compression paddles 14 may comprise a transparent polymeric material. Alternatively, compression paddles 14 may be made of thin carbon fiber. There can be multiple varieties of compression paddles (as in mammography) suitable for use herein, of which some are solid, and some include apertures of various sizes for biopsy or surgery access. Compression paddles 14 need not be planar. They may, for example, be contoured (for example, arced or curved) to better conform to the shape of breast 4. Gamma cameras 15 can also be contoured (for example, arced or curved), especially when composed of modular pixelated detectors, to fit the curvature of compression paddles 14.

Compression paddles 14 and gamma cameras 15 are each mechanically attached by separate support arms (16 and 17, respectively) to the MBI gantry 11. Compression paddles 14 are typically mechanically independent of the gamma cameras 15. Compression paddle support arms 16 are directly connected to gantry 11. Gamma camera support arms 17 can position gamma cameras 15 in direct contact with thin compression paddles 14, when present, so that gamma cameras 15 are as close as possible to breast 4, which will optimize the image quality (as will be apparent to those skilled in the art). However, in the illustrated embodiment gamma cameras 15 do not directly contact breast 4 and do not provide any compressive force on breast 4. However, an upper compression paddle 14 is required only for MBI-guided biopsy. When the corresponding upper gamma camera 15 is moved away from the region of the upper breast, the upper compression paddle 14 maintains the breast immobilization and provides an aperture for a biopsy grid.

A lower compression paddle 14 is not required for a biopsy in the upper half of a breast or the axilla. However, a lower compression paddle 14 may be used when the hot spot to be sampled by biopsy or surgery is in the lower half of the breast and the patient is placed in an upright sitting position. If one or both compression paddles 14 are absent, then the corresponding gamma cameras 15 must directly contact the breast and provide the mild compressive force required to immobilize the breast 4. As will be apparent to those skilled in the art, the configuration of system 10 with compression paddles 14 places the gamma cameras 15 slightly further away from breast 4, typically by a fraction of a centimeter, but with significant advantages in clinical practice. The typical design of a compression paddle 14, as is well-known by those skilled in the art, is similar in geometry to a cut-away of the bottom of a box. That is, the paddle includes a bottom surface that contacts breast 4 and there are four perpendicular sides to give mechanical strength to the paddle. Those four sides and bottom constitute a "well" into which gamma camera 15 can be designed to fit loosely or readily removably. In several embodiments, compression paddles 14 are each connected by at least two support arms 16 to the compression mechanism of the gantry 11. Gamma cameras 15 are each connected by support arms 17 to the compression mechanism of gantry 11.

Those skilled in the art will appreciate that the force compressing the breast, whether applied by compression paddles 14 or gamma cameras 15, should be carefully measured and controlled, regardless of the angle of the gantry. In general, for MBI the compressive force is less than ⅓ that of mammography.

Figure 2:
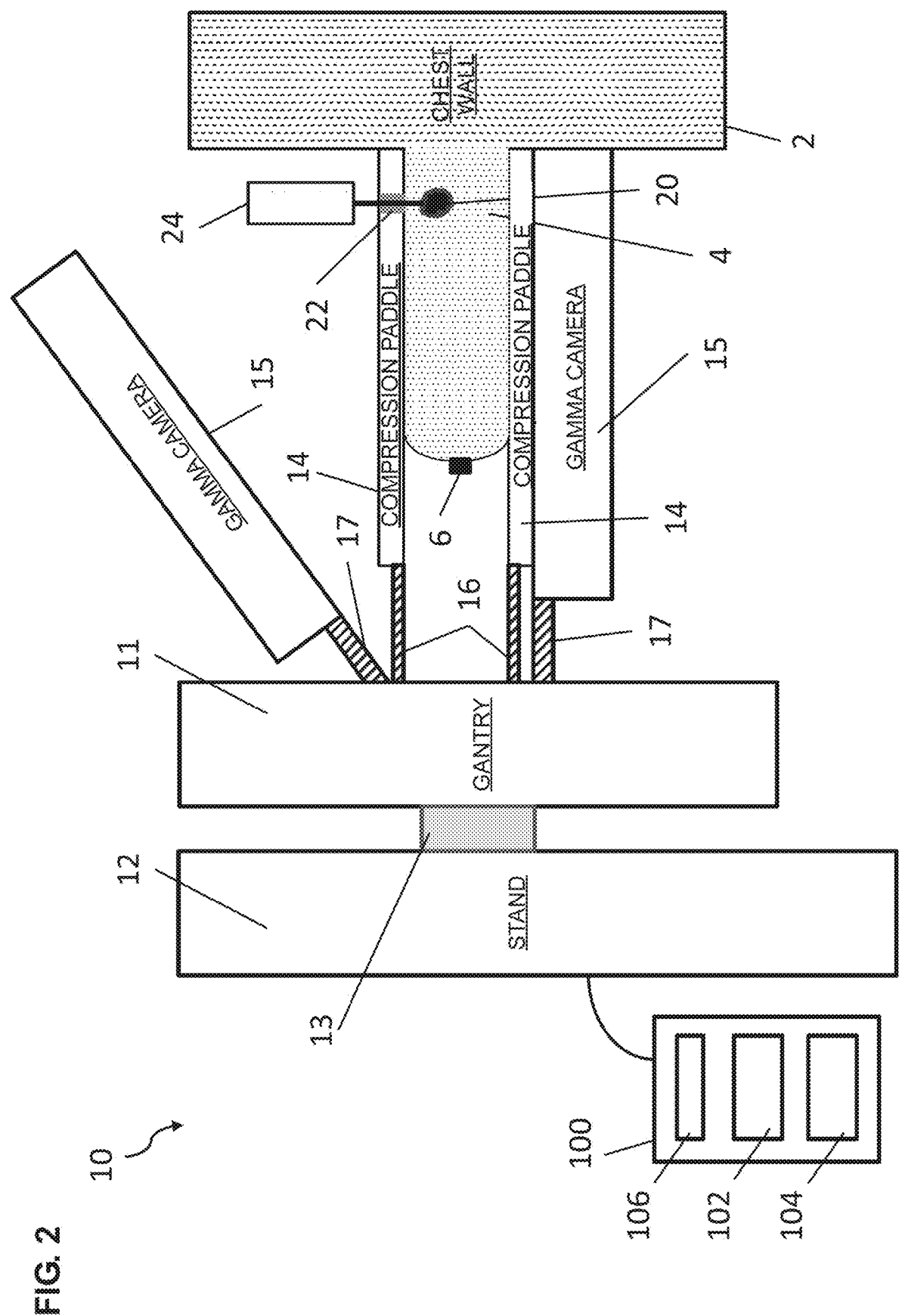
FIG. 2 illustrates MBI system of FIG. 1 with the repositioning of the upper gamma camera, for example, to allow room for biopsy or surgery, wherein a needle or core biopsy device is shown sampling a hot spot in accordance with embodiments hereof.

FIG. 2 illustrates an embodiment of MBI system 10 of FIG. 1 used in connection with the methodologies hereof. The figure shows a cross-sectional side view of MBI system 10 during an MBI-guided biopsy procedure. Support arms 17 of gamma camera 15 may be articulated to tilt, rotate, or otherwise move one or both of gamma cameras 15 out of the immediate vicinity of breast 4 when not imaging. This ability provides an advantage during the positioning of breast 4 prior to imaging and during biopsy or surgery guidance. Compression paddles 14 are typically clear, unless they are made of carbon fiber, and they often have an aperture (for example, a rectangular aperture) or apertures to accommodate a biopsy needle locator grid. Thus, with the gamma cameras 15 out of the way, the technician can see the breast that she is positioning for imaging.

In FIG. 2 upper gamma camera 15 is shown tilted out of the area above the breast to make room for ultrasound- or MBI-guided biopsy. The tilting could be manually controlled or automated and computer controlled. Of course, proper locking and safety mechanisms should be provided to keep heavy gamma cameras 15 fixed in place, whether tilted or in contact with compression paddles 14. In FIG. 2, a hot spot 20 is depicted in breast 4 and a biopsy device 24 is depicted with a needle traversing an aperture 22 in the compression paddle 14. The biopsy device 24 may, for example, represent fine needle aspiration, core needle (such as spring-loaded or vacuum-assisted versions), or surgical biopsy. The illustrated single opening 22 in compression paddle 14 represents an entire grid of apertures. After the 3D position of a hot spot is identified, electronic circuitry 100 may determine which grid contains the (x, y) position of the hot spot. A block with small holes is placed in the identified grid aperture 22. Electronic circuitry 100 identifies which hole in the block to use and the depth to insert the needle (z position). Of course, other embodiments may not use the prior art grid and block locator mechanisms. For example, an ultrasound coupled to the MBI system could be used to guide biopsy device 24 to the MBI-identified hot spot.

Figure 3C:
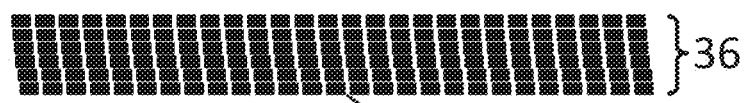
FIG. 3C further illustrates schematically the principal of the Variable-Angle Slant Hole (VASH) collimator in accordance with embodiments hereof.
Figure 3B:
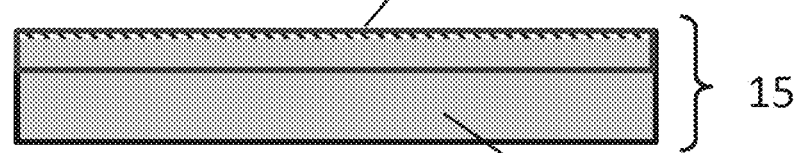
FIG. 3B illustrates schematically two major components of the gamma camera, the detectors and the collimator.
Figure 3A:
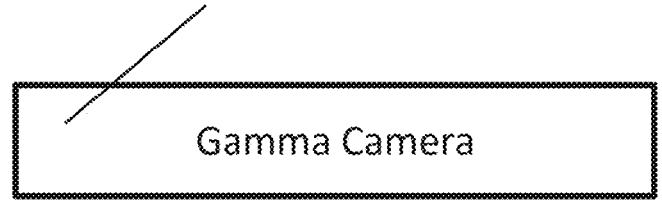
FIG. 3A illustrates schematically an isolated view of the lower gamma camera from FIGS. 1 and 2.

FIGS. 3A through 3C shows more detail of lower gamma camera 15. FIG. 3A illustrates gamma camera 15 isolated from system 10 of FIGS. 1 and 2. FIG. 3B shows that each gamma camera 15 comprises a gamma photon detector 32 and a collimator 34. There are two types of gamma photon detectors 32 currently deployed by the several companies that offer commercial MBI systems. The older technology utilizes a scintillator (typically NaI or CsI, monolithic or pixelated) with a photodetector (typically avalanche photodiodes [APDs] or photomultiplier tubes [PMTs]). The newer technology utilizes direct-conversion solid-state semiconductor detectors (typically CdZnTe [CZT] or CdTe). The devices, systems and methods hereof apply to single detector MBI systems as well as the more sensitive dual-detector MBI systems. In another type of MBI device, both upper and lower detector assemblies of gamma cameras 15 include gamma photon detectors 32 configured for coincidence event detection as part of a Positron-Emission Mammography (PEM) system, which requires no physical collimator. In that case, gamma photon detectors 32 utilize a scintillator (typically LYSO or other PET scintillator) and a photodetector (typically APDs or silicon photomultipliers [SiPMs]).

FIG. 3C illustrates a simplified schematic of special collimator referred to as a Variable-Angle Slant Hole (VASH) collimator. Such a collimator may, for example, include a stack of thin (for example, tungsten) leaves or plates 36, each including an array of (for example, etched) square holes that align with the holes array of other sheets. A mechanism is provided to induce a shear-like motion to the stack of plates to produce a slant hole collimator. FIG. 3C shows only an illustrative handful of plates and does not show the relative size of the holes and the remaining tungsten septa between holes. As an example, a prototype VASH collimator was constructed for the studies hereof with up to 50 leaves, wherein each leaf was 0.25 mm thick for a total stack thickness of 12.5 mm. The holes were 1.35 mm square holes and the septa were 0.25 mm. One significant advantage of a VASH collimator is that it avoids the need for collimator exchange as has been the common practice in Nuclear Medicine. A VASH collimator can be used for ordinary imaging (slant angle=0 degrees), such as supplemental screening, diagnosis, or theranostics. Without anything more than a software command, the variable slant angles of a VASH collimator can be set for biopsy guidance (typically two images at 15 to 60 degrees spread in slant angles).

FIG. 4B illustrates a VASH collimator mechanism for inducing a shearing-like, or sliding relative motion in/between the tungsten leaves or plates thereof to vary the slant angles which was developed by the Jefferson National Accelerator Lab in Newport News, Virginia and which is described in U.S. Pat. No. 9,711,251, the disclosure of which is incorporated herein by reference. FIG. 4B is derived from U.S. Pat. No. 9,711,251. VASH collimator 200 of FIG. 4B includes a plurality of stacked leaves or plates 210, guided by rails 205, of which an upper leaf or plate 210 includes a face 212 which is visible in the top view of FIG. 4B. Each leaf or plate 210 includes an array 214 of apertures 216. Four push/pull blocks 220 are driven by lead screws 230 (supported by pillow blocks 234). Lead screws 230 include right-hand threads 230a and left-hand threads 230b on opposing sides of pillow block 234. When activated, motors 240 drive lead screws 230, and blocks 220 will induce shearing motion to the stack of tungsten leaves 210 while keeping square holes/apertures 216 aligned along the desired slant angle. As described above, a working prototype collimator 200 including 50 leaves was studied in the studies hereof.

Figure 5:
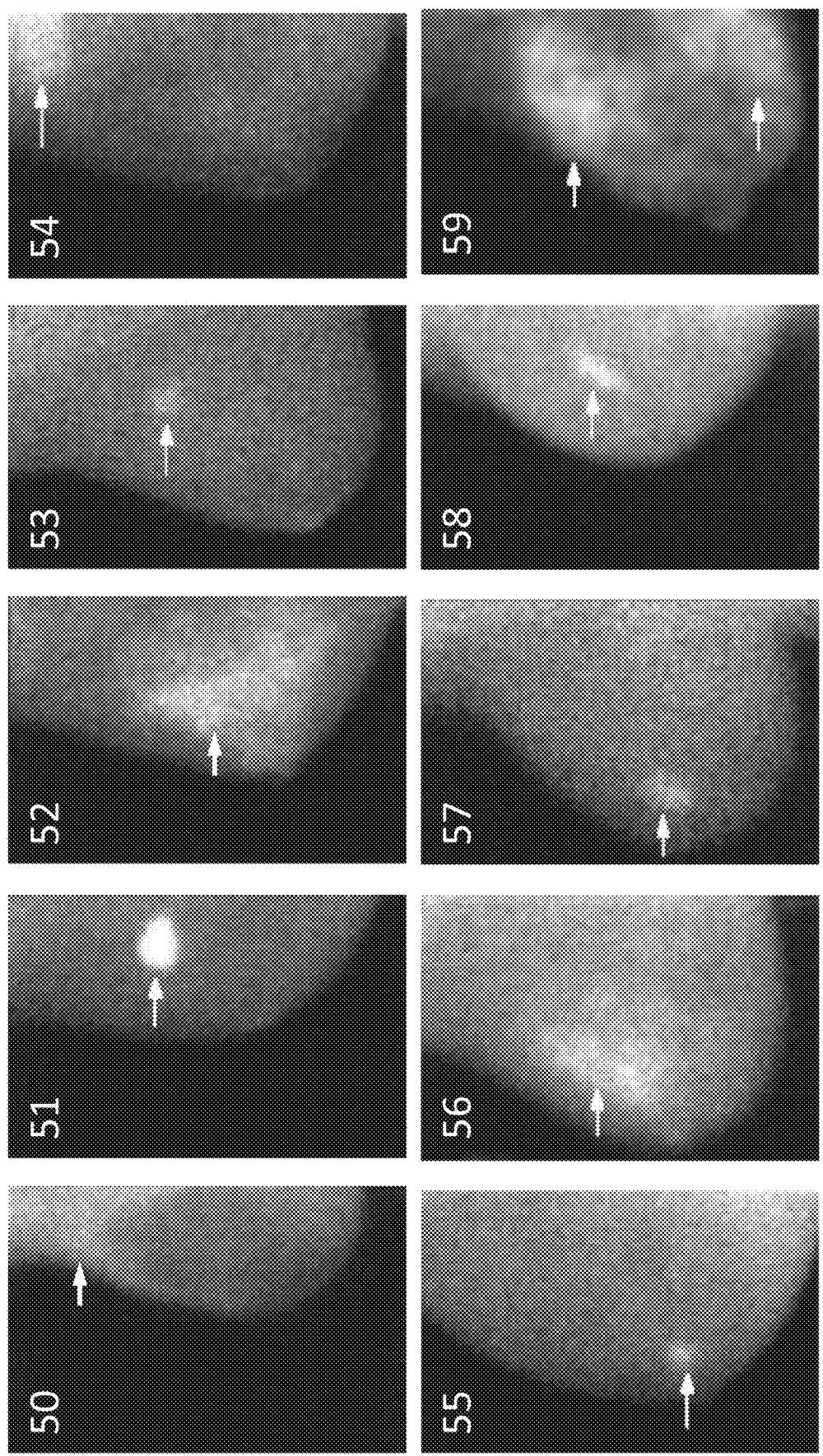
FIG. 5 is an illustration of ten right breasts of women with dense breasts, whose MBI reveals a hot spot that required biopsy, wherein, in six of these ten cases the hot spot is more punctate while the other four are more diffuse, and wherein the arrows illustrate potential biopsy targets.

FIG. 5 illustrates typical molecular breast images 50-59 that exhibit focal or diffuse regions of significantly increased tracer uptake ("hot spots") with respect to background parenchyma (the remainder of the breast tissue image other than any identified hot spots). In these images a white arrow has been overlaid to identify the suspicious hot spot to be biopsied. Each of these images provided by courtesy of the Mayo Clinic was acquired with an injection of 6-8 mCi of Tc99m-Sestamibi and each image was acquired for 10 minutes.

Figure 6:
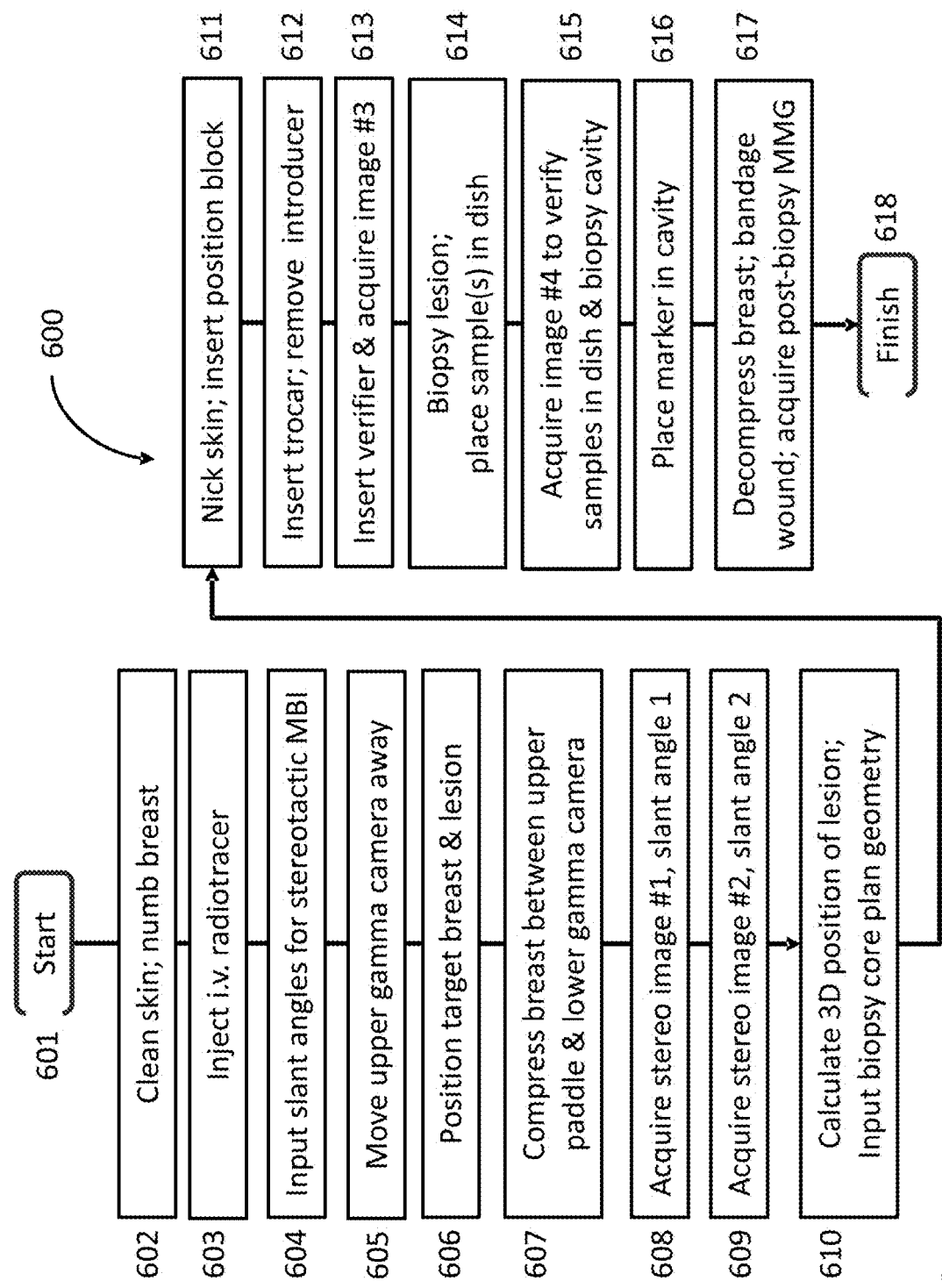
FIG. 6 illustrates an embodiment of a flowchart for MBI-guided breast biopsy in accordance with embodiments hereof.

FIG. 6 illustrates a representative embodiment of a clinical protocol or methodology 600 for MBI-guided biopsy. In action or step 601 the MBI-guided biopsy procedure starts with patient preparation, typically outside the MBI imaging and biopsy procedure room. The patient will typically remove her shirt/top and bra, then don a patient gown open at the front. A breast technician or nurse will typically insert an i.v. port, usually in an arm. In action or step 602, the breast radiologist who will perform the biopsy typically will mark the skin in the approximate location of the needle entry for the planned approach to each hot spot to be biopsied. Note that the radiologist may plan to enter the top of the breast to reach a hot spot located in the lower half of the breast. The radiologist cleans the skin and injects anesthetic to numb the breast and reduce bleeding. In action or step 603 the radiotracer is injected through the previously placed port. For supplemental diagnostic and screening MBI, doses of Tc99m-Sestamibi are typically 6-8 mCi. However, for biopsy a 20 mCi dose is more common. The larger dose reduces the imaging time to a few minutes.

For action or step 604, the two slant angles for stereotactic MBI may typically be entered before the patient is brought to the MBI room. The slant angles or a plane in which the slant angles lie (as represented by arrow A in FIG. 4B) are desirably in a generally left-right or medial-lateral direction for biopsy guidance as indicated in (see FIGS. 4A and 4B). As used herein a generally left-right or medial-lateral orientation refers to an orientation within 30 degrees of the left-right or medial-lateral orientation. More typically, that orientation will be within 5 degrees, or within 3 degrees of the left-right or medial-lateral orientation. While it is possible to use the currently practiced Anterior-Posterior (A/P) direction for slant angle orientation, there is much more risk of overwhelming the breast image with views of internal organs, such as the heart and bladder. Furthermore, a portion of the breast next to the chest wall may be missed by operating a VASH collimator in the A/P direction, as explained elsewhere herein. Additionally, there is more room for VASH hardware such as a drive motor in the generally Left-Right or medial-lateral orientation. In action or step 605 upper gamma camera 15 is moved away from the patient breast biopsy area so that the breast can be visualized during placement, and so that gamma camera 15 will not interfere with the biopsy procedure.

Upon entering the MBI exam room for step 606 the technician seats the patient in the examination chair and positions the target breast and hot spot in the MBI system. The target mark will be approximately centered left-right or laterally in upper compression paddle 14 aperture. The biopsy grid should be placed into the aperture of upper compression paddle 14. In action or step 607 the breast will then be compressed between upper compression paddle 14 and lower gamma camera assembly 15. It is also possible, but usually unnecessary to use two compression paddles 14. Note that only a single, lower gamma camera 15 with a VASH collimator 36 is necessary for determining hot spot location. Upper gamma camera 15 also may be used, but it is not required. If upper gamma camera 15 is used, the exam time will be lengthened because it will be moved into and out of the procedure field multiple times.

In action or step 608 the first stereo image is acquired with VASH collimator 36 on lower gamma camera 15 set at slant angle $\theta_1$ (typically 15 degrees, but which can range between about $-30$ and $+30$ degrees). In action or step 609 the second stereo image is acquired with VASH collimator 36 on the lower gamma camera 15 set at $\theta_2$ (typically $-15$ degrees but which can range between about $-30$ and $+30$ degrees). The angular spread between the two slant angles is typically between about 20 and 60 degrees. Note that the two slant angles do not need to be symmetric about the normal direction (perpendicular) to gamma camera 15. If the slant angles are not symmetric, the 3D position calculation is only slightly more complicated, as shown below.

In action or step 610, the electronic circuitry/computer will identify the center of the hot spot on the images using the two stereo images from lower gamma camera 15. Only if upper gamma camera 15 was used, the two normal images from upper gamma camera 15 may also be used to identify the (x, y) position of the target hot spot. The radiologist will have the opportunity to accept or reject the computer identification of the hot spot center as the target for biopsy. The radiologist may choose to set the biopsy target elsewhere, such as in a large diffuse hot spot. When the target center is chosen, the computer calculates the 3D position of the target. Lower gamma camera 15 provides two stereo images with preselected parallax shift on each. If the center of the hot spot is $(x_1, y_1)$ and $(x_2, y_2)$ on the two images, respectively, and the slant angles are $\theta_1$ and $\theta_2$, respectively, then $$x = [(x_1 + x_2)/2] + [(x_2 - x_1)/2] \cdot [\sin(\theta_1 + \theta_2)/\sin(\theta_1 - \theta_2)],$$

$$y = (y_1 + y_2)/2,$$

and $$z_A = (x_1 - x_2)/(\tan(\theta_1) - \tan(\theta_2)).$$

Note that these expressions simplify when the slant angles are symmetric, i.e., $\theta_2 = -\theta_1$:

$$x = (x_1 + x_2)/2,$$

$$y = (y_1 + y_2)/2,$$

and $$z_A = (x_1 - x_2)/(2 * \tan(\theta_1)).$$

Here $z_A$ is the apparent depth of the hot spot with respect to the face of the lower CZT detector. This can be calibrated to the depth $z_N$ from the top of the grid to the hot spot center, which is the depth of relevance to the biopsy needle. The various calibrations comprise:

$$z_N = z_G + z_B + z_0 - z_A.$$

Here $z_G$ is the thickness of the grid block, $z_B$ is the thickness of the compressed breast, which is the distance between two compression paddles 14, and $z_0$ is the sum of the thickness of a VASH collimator plus lower compression paddle 14 plus any air gaps plus the effective interaction depth in the CZT (typically about 1 mm in our experience).

Since the 3D position of the biopsy target is now known, the next part of action or step 610 is to input to the computer the biopsy core plan geometry. The radiologist may choose to sample the hot spot with fine needle aspiration, core needle (spring-loaded or vacuum-assisted, for example), or by surgical biopsy. The radiologist might plan to sample cores beyond the upper and lower limits of the hot spot and in multiple directions (axial rotation of the core needle sampler). The computer will identify which grid aperture should receive the block and which hole in the block should receive the needle.

In action or step 611 the radiologist will typically nick the skin at the trocar entry point. A position block will be inserted into the computer-identified grid aperture. In action or step 612 a trocar will be set to depth $z_N$ (or other depth, depending on the core plan geometry chosen). The trocar will be inserted to the marked depth and the inner trocar ("introducer") will be removed to be replaced first by the verifier (action or step 613) and then the biopsy needle (action or step 614).

Action or step 613 is a verification that the trocar is in the intended location by imaging a radioactive line source or point source or multi-point line source. This action or step may be skipped, but it is recommend that it be performed. The line source must be inside a sterile tube, since it will enter the patient's breast tissue. One way to achieve a sterile line source is to take a piece of sterile plastic tubing, seal one end, fill the tubing with Tc99m-Sestamibi, and seal the other end. This procedure has the advantage of easy disposability after decaying for several days. If such an action or step is performed, then the verifier is inserted, and the third image is acquired. The current slant angle ($\theta_2$) does not need to be changed for this verifier image. The radiologist confirms that the line source (representing the needle position) is in the intended position with respect to the hot spot. The verifier is removed and may be returned to the radiotracer supplier to handle disposal.

Action or step 614 is MBI-guided biopsy, where the outer trocar, which is still in place in the patient's breast, will guide the needle to the hot spot for biopsy sampling. Multiple cores may be sampled and each may be placed, in order, into a sample dish. In a number of embodiments of methods hereof, the sample dish, when all samples have been taken, can be attached to lower gamma camera 15 for verification imaging. In action or step 615 an MBI verification image #4 is acquired of at least one of the sample(s) taken and the breast. If the biopsy was performed in the correct location, one or more of the samples should contain areas that are "hot" with a higher count density and the biopsy cavity should be "cool" or "warm" with a lower count density than in images #1, #2, and #3, since hot spot samples were removed from the cavity. In step 616, when the radiologist is satisfied that all core samples have been taken, then a radiographic marker may be placed in the cavity.

Action or step 617 is to decompress the breast and bandage the wound (pressure is normally applied before or after bandaging). If desired by the radiologist, a post biopsy mammogram with light compression may be taken to document the position of the marker and biopsy cavity.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A molecular imaging method for guidance of a biopsy or a surgical procedure, comprising:
   selecting and inputting two different slant angles for stereotactic molecular imaging of an area indicative of a lesion;
   positioning a patient to whom a radiotracer has been administered in a molecular imaging system comprising a solid-state gamma camera and a variable-angle slant hole (VASH) collimator;
   acquiring two stereotactic molecular images with the VASH collimator, each of the two stereotactic molecular images being acquired when the VASH collimator is adjusted to a different one of the two different slant angles, the VASH collimator being positioned such that the two different slant angles are in a plane generally parallel to a coronal plane of the patient;
   calculating a 3D position of the area indicative of a lesion; and
   performing a molecular image-guided biopsy procedure on the basis of the calculated 3D position.

2. The method of claim 1 wherein the VASH collimator is positioned such that the two different slant angles are in a plane within 5 degrees of parallel to the coronal plane of the patient.

3. The method of claim 1 wherein the two different slant angles have an angular spread of 10 to 60 degrees.

4. The method of claim 3 wherein the VASH collimator comprises a stack of thin leaves, each of the leaves comprising an array of square holes, and a mechanism for positioning the leaves to align the square holes at the two different slant angles.

5. The method of claim 1 wherein the performing of the molecular image-guided biopsy procedure comprises compressing tissue via a compression paddle comprising an aperture therein and movement of a second solid-state gamma camera, which is movable in and out of connection with the compression paddle, to allow access to the aperture.

6. The method of claim 5 wherein the performing of the molecular image-guided biopsy procedure further comprises acquiring a verification molecular image of a pathway to approach the hot spot.

7. The method of claim 1 wherein the molecular imaging method comprises molecular breast imaging (MBI), single photon emission (SPE) planar imaging, single photon emission computed tomography (SPECT), or positron emission tomography (PET).

8. The method of claim 1 wherein the molecular imaging system further comprises a second or third solid-state gamma camera, each gamma camera comprising one of a parallel-hole collimator, a slant-hole collimator, a focusing collimator, a VASH collimator, and a multiple pinhole collimator.

9. The method of claim 1 further comprising placing a cavity marker in a breast biopsy procedure and acquiring a post-biopsy mammogram.

10. The method of claim 1 wherein electronic circuitry is in communicative connection with the solid-state gamma camera and with the VASH collimator, wherein the electronic circuitry is configured to control slant angles of the VASH collimator and to control the solid-state gamma camera to acquire a molecular image at each of the two different slant angles, which are input into the electronic circuitry, the electronic circuitry being further configured to calculate the 3D position of the area indicative of a lesion from the molecular images at each of the two different slant angles.

11. A molecular imaging method for guidance of a biopsy or a surgical procedure, comprising:
    selecting and inputting two different slant angles for stereotactic molecular imaging of an area indicative of a lesion;
    positioning a patient to whom a radiotracer has been administered in a molecular imaging system comprising a solid-state gamma camera and a variable-angle slant hole (VASH) collimator;
    acquiring two stereotactic molecular images with the VASH collimator, each of the two stereotactic molecular images being acquired when the VASH collimator is adjusted to a different one of the two different slant angles, wherein the VASH collimator is positioned such that the two different slant angles are in a plane generally parallel to a coronal plane of the patient;
    calculating a 3D position of the area indicative of a lesion;
    performing a molecular image-guided biopsy procedure on the basis of the calculated 3D position; and
    acquiring a confirmation molecular image of at least one of one or more samples taken and a procedure cavity.

12. The method of claim 11 wherein the two different slant angles have an angular spread of 10 to 60 degrees.

13. The method of claim 11 wherein the VASH collimator comprises a stack of thin leaves, each of the leaves comprising an array of square holes, and a mechanism for positioning the leaves to align the square holes at the two different slant angles.

14. The method of claim 11 wherein electronic circuitry is in communicative connection with the solid-state gamma camera and with the VASH collimator, wherein the electronic circuitry is configured to control slant angles of the VASH collimator and to control the solid-state gamma camera to acquire a molecular image at each of the two different slant angles, which are input into the electronic circuitry, the electronic circuitry being further configured to calculate the 3D position of the area indicative of a lesion from the molecular images at each of the two different slant angles.

* * * * *